United States Patent [19]

Nelson

[11] Patent Number: 5,671,529
[45] Date of Patent: Sep. 30, 1997

[54] METHOD OF FORMING A MOLDED PULSE OXIMETER SENSOR

[75] Inventor: Dale Nelson, Corona, Calif.

[73] Assignee: Sensormedics Corporation, Yorba Linda, Calif.

[21] Appl. No.: 473,733

[22] Filed: Jun. 7, 1995

Related U.S. Application Data

[63] Continuation of Ser. No. 267,849, Jun. 29, 1994, Pat. No. 5,425,360, which is a continuation of Ser. No. 919,220, Jul. 24, 1992, abandoned.

[51] Int. Cl.⁶ .................................................. H01R 43/00
[52] U.S. Cl. ............................. 29/825; 128/633; 128/666
[58] Field of Search ............................ 29/883, 884, 825; 264/263, 274, 272.15

[56] References Cited

U.S. PATENT DOCUMENTS

| | | | |
|---|---|---|---|
| 3,574,815 | 4/1971 | Segerson | 264/274 X |
| 4,684,202 | 8/1987 | House et al. | 264/263 X |
| 4,701,999 | 10/1987 | Palmer | 264/274 X |
| 4,821,413 | 4/1989 | Schmitt et al. | 264/272.15 X |

*Primary Examiner*—Carl J. Arbes
*Attorney, Agent, or Firm*—Lyon & Lyon LLP

[57] ABSTRACT

A pulse oximeter sensor apparatus which is sealed against liquid penetration during its formation by overmolding, and methods for overmolding. The pulse oximeter sensor apparatus disclosed comprises a preform first section, oximeter sensor components, and an overmolded second section bonded to the preform first section during the overmolding process to form a liquid resistant seal comprising a mechanical bond of overlapping elements.

10 Claims, 2 Drawing Sheets ial hemoglobin oxygen saturation. Such oximeters are described, e.g., in U.S. Pat. No. 4,824,242, which is incorporated herein by reference.
5,671,529

METHOD OF FORMING A MOLDED PULSE OXIMETER SENSOR

This is a continuation of application Ser. No. 08/267,849 filed on Jun. 29, 1994, now U.S. Pat. No. 5,425,360, which is a continuation of Ser. No. 07/919,220 filed on Jul. 24, 1992, now abandoned.

BACKGROUND OF THE INVENTION

The field of the present invention is sensor apparatus for pulse oximetry.

Pulse oximetry provides a means of non-invasively measuring oxygen saturation of arterial blood for purposes of monitoring and evaluating the physical condition of a patient under medical care and to avoid patient hypoxemia. Pulse oximetry functions by positioning a pulsating arterial vascular bed (such as that in a patient's finger or ear lobe) between a two-wavelength light source and a detector. The pulsating vascular bed, by expanding and relaxing, creates a change in the amount of light passing through at each wavelength. Oxyhemoglobin and reduced hemoglobin differ in their light absorption characteristics. The varying amounts of light from the light source passing through the vascular bed are received by the detector as a waveform, whose signal is processed electronically by a pulse oximeter into a measurement of arterial hemoglobin oxygen saturation. Such oximeters are described, e.g., in U.S. Pat. No. 4,824,242, which is incorporated herein by reference.

A sensor apparatus, containing the light source, the detector, and connecting wiring or cables, is used to position the light source and detector components in proper relation to each other at an appropriate body site. For example, the light source may be positioned on one side of a patient's finger, with the detector positioned directly opposite the light source on the other side of the finger. Cables and wiring connect the light source and detector at the patient site, and transmit the waveform signal to the oximeter for processing. The light source, the detector, and their connecting wires have typically been secured to a support which facilitates proper placement of the light source and detector in relation to each other and at the desired site on the patient. For example, the light source, detector, and connecting cables have been attached to a flexible wrap material, which is wrapped around and temporarily secured to a body site, such as a finger. Such a sensor apparatus generally is a single use, disposable item due to its direct contact with the patient. A drawback of such a disposable oximeter sensor apparatus is its relatively high cost per use.

Alternately, sensor components (including the light source, detector, and connecting wires) have been mounted and sealed into, for example, a molded shell which can be disinfected and reused in multiple applications and among different patients. However, such a reusable oximeter sensor apparatus must be relatively durable to withstand multiple attachments, and the sensor components must be sealed within the molded shell so that application of liquid disinfectant to the surface of the shell by wiping or immersion will not result in moisture reaching and damaging the sensor components. Further, the molding process must be accomplished without the use of excess or prolonged high temperature which would damage the sensor components.

As a result, existing reusable oximeter sensors have been relatively costly since their manufacture is labor and/or time intensive. For example, such reusable sensors have been manufactured by first molding two shell halves, enclosing the sensor components between the halves in proper position, and then gluing the halves together to seal out moisture, a time and labor intensive process.

Alternatively, reusable oximeter sensors have been manufactured utilizing a silicone overmolding process, in which the sensor components are positioned within a first premolded silicone half shell, and then encased and sealed as silicone is injected in an overmolding step to complete the molded shell. Due to the properties of the silicone used, the two portions of the completed molded shell seal to each other. However, the cycle time for this overmolding operation is typically 25–40 minutes, depending on the specific type of silicone and its curing temperature. The curing temperature must be kept low, resulting in the relatively long cure time, since excess heat will destroy the cable and optical components which comprise the active sensor components. Further, given such long cycle times, each base mold can produce only relatively few molded sensors per day, requiring large capital expenditures for multiple base molds or tools to achieve significant daily volume production of sensors.

SUMMARY OF THE INVENTION

The present invention is directed to oximeter sensors which can be disinfected and reused. The oximeter sensors of the present invention are simultaneously formed and sealed utilizing overmolding without requiring lengthy cure times, and enclose sensing components. The oximeter sensor comprises a preformed first section and an overmolded second section which is sealed to the first section utilizing a molded mechanical bond of overlapping elements.

Accordingly, it is an object of the present invention to provide a low cost, reusable oximeter sensor utilizing an overmolding process.

A further object of the present invention is to provide a method for overmolding a reusable, low cost oximeter sensor.

Other and further objects and advantages of the present invention will be evident hereinafter.

BRIEF DESCRIPTION OF THE DRAWINGS

FIG. 1 shows a preferred embodiment of the present sensor apparatus invention.

FIG. 2a shows a cross-sectional view of FIG. 2 taken along line 2a—2a.

DETAILED DESCRIPTION OF THE PREFERRED EMBODIMENT

Figure 1A:
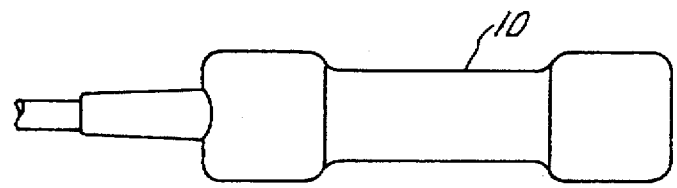
FIG 1a shows the back side of the apparatus.
Figure 1B:
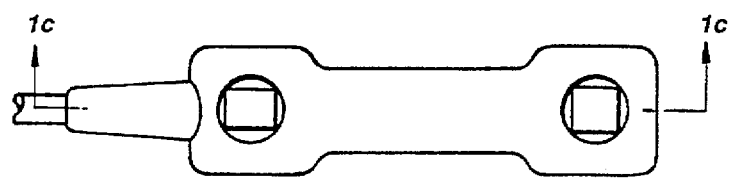
FIG. 1b shows the front or patient side of the apparatus.
Figure 1C:
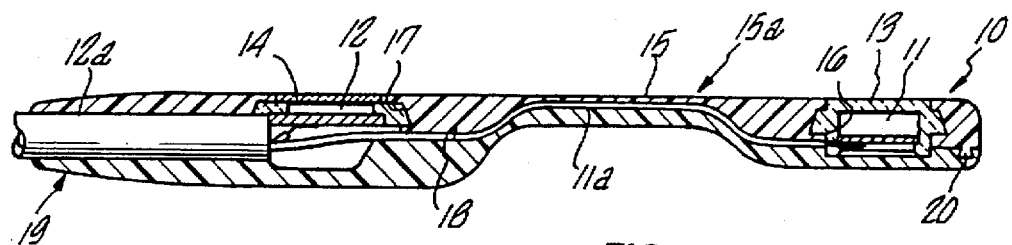
FIG. 1c shows a cross-sectional view of FIG. 1b taken along line 1c—1c.

Turning in detail to the drawings, FIGS. 1a, 1b, and 1c illustrate a molded pulse oximeter sensor apparatus 10 of the present invention. As shown in FIG. 1c, the active sensing components comprising the light source ceramic 11, detector ceramic 12, and connecting wires 11a are contained within the completed sensor apparatus 10. Cable 12a connects these active elements to a pulse oximeter. Cable 12a may extend from the sensor apparatus 10 in various directions and orientations. The light source 11 and detector 12 are mounted into pre-molded clear polyvinylchloride (PVC) window compartments 13 and 14 such that the light source and detector each physically interlock into their respective window compartments. These window compartments can be molded by those skilled in the art using PVC materials such as, e.g., Maclin VM-3270 clear.

Figure 2:
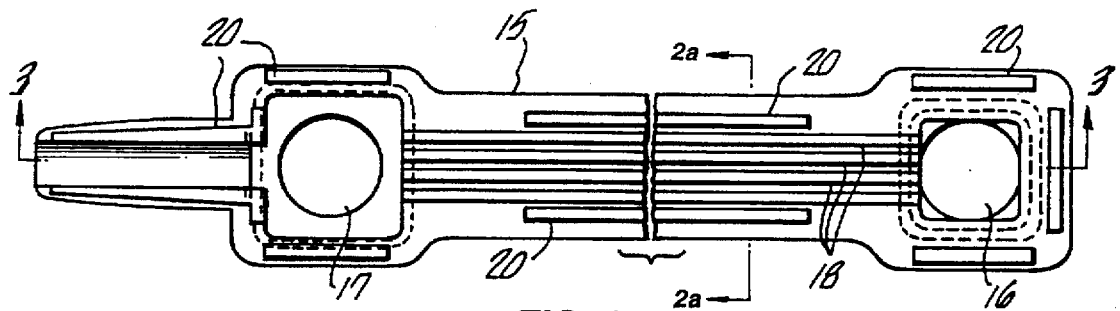
FIG. 2 shows the interior surface of the premolded preform first section.
Figure 3:
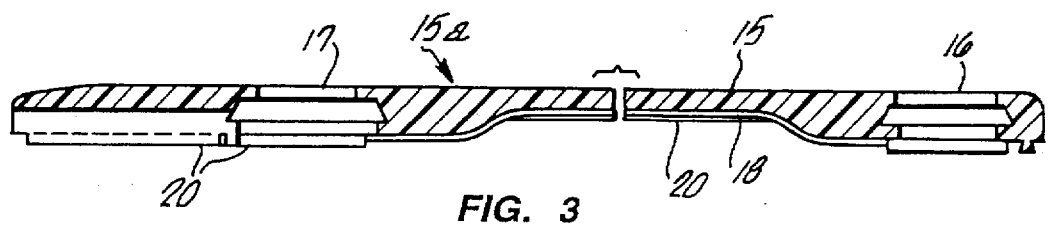
FIG. 3 shows a cross-sectional view of the premolded preform first section of FIG. 2 taken along line 3—3.
Figure 2A:
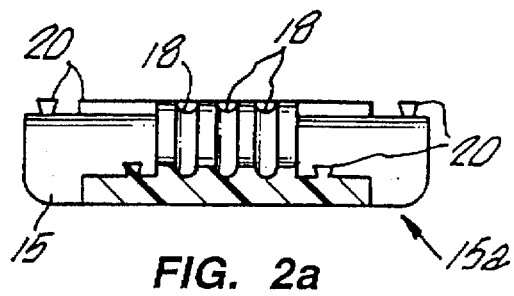
Figure 5A:
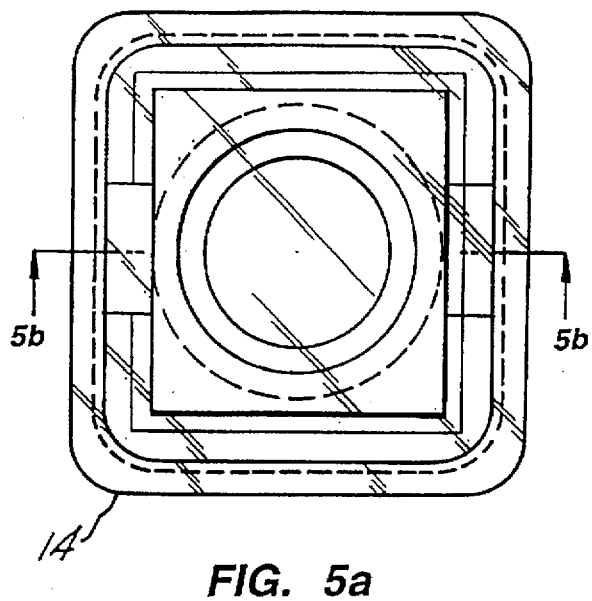
FIG. 5a shows the sensor detector window.
Figure 4A:
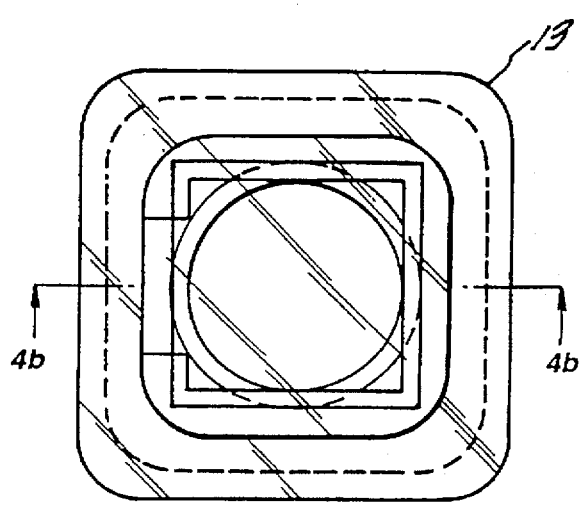
FIG. 4a shows the sensor light source window.
Figure 5B:
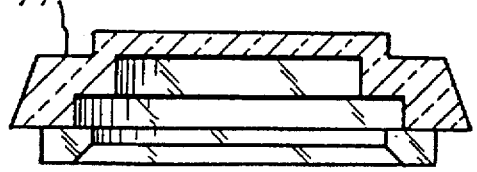
FIG. 5b shows a cross-sectional view of FIG. 5a taken along line 5b—5b.
Figure 4B:
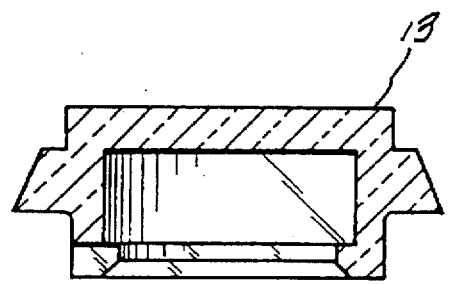
FIG. 4b shows a cross-sectional view of FIG. 4a taken along line 4b—4b.

Window compartments 13 and 14 are mounted into a premolded preform first section 15. These window compartments are shown in FIGS. 4a, 4b, 5a, and 5b. The premolded preform first section 15 may be molded, using techniques known to those of skill in the art, from an appropriate 38 durometer medical grade PVC material, such as, e.g., Maclin Apex-3500 R40 white. The premolded preform first section 15 contains a cavity 16 for the light source window compartment 13 and a cavity 17 for the detector window compartment 14. Each cavity is molded to have locking features for positive mounting and sealing of the windows into the premolded perform first section 15. The features of the window cavities 16 and 17 are shown in FIGS. 2 and 3. The insertion of both the light source 11 and detector 12 into their respective window compartments 13 and 14, and the insertion of window compartments 13 and 14 into their respective cavities 16 and 17 in the premolded preform first section 15 is facilitated by the fact that both the PVC windows and the preform first section are fairly compliant and permit stretching of the interlocking features during insertion. Once inserted, the compliant PVC material returns to its initial molded shape. The window compartments 13 and 14 extend to the exterior surface or patient side 15a of the preform first section 15, as shown in FIGS. 1b and 1c.

Wires 11a connecting the light source 11 are mounted into wire guides 18 that locate and position the wires 11a along the interior surface of the preform first section 15 for proper orientation and alignment of the wires during the overmolding operation. The preform first section 15 employs the above mentioned wire guides 18 which transverse the distance between the detector 11 and the light source 12 ceramics to prevent movement of or damage to the wires 11a during the overmolding operation. These wire guides 18 may comprise grooves, or raised ridges, or both, along the interior surface of the preform first section In an alternate embodiment, the light source 11, detector 12, and connecting wires 11a may instead be contained in a one-piece Kapton flex circuit formed from high strength, high temperature plastic material. This flex circuit is positioned along the interior surface of the preform first section 15, and the light source and detector portions of the flex circuit again interlock into pre-molded clear PVC window compartments which are mounted into the preform first section 15.

The requirements of signal strength for the light source 11 may cause production of excess heat, which could burn a patient. The mounting of the light source 11 within its window compartment 13 provides a buffer between the light source 11 and the patient contact point, protecting the patient from excess heat, as well as sealing the light source ceramic 11 from the patient side 15a of the preform first section 15. Similarly the window compartment 14 for the detector 12 is utilized for sealing and protecting the detector ceramic 12, as well as providing an additional patient buffer against electrosurgical grounding discharges. The window compartment 14 also eliminates any need for secondary operations of backfilling the cavity 17, as would otherwise be required to secure and seal the detector 12 into the preform first section 15.

In the overmolding operation, the overmolded second section 19 is formed by injection molding, preferably using the same PVC material as is used to form the preform first section 15. The preform first section 15 and sensor components are properly positioned and placed into a base mold. Overmolding material (PVC) is injected to form the overmolded second section 19 and to enclose the sensor components between the preform and overmolded sections and to bond these two sections together, forming the completed oximeter sensor apparatus 10. During the overmolding step, the cable 12a is also surrounded by the injected PVC material at the point the cable 12a exits the molded sensor apparatus. In the preferred embodiment, the major mold base is designed so that it accommodates insertion of a separate mold system, called coffin molds. These coffin molds hold the preform assembly, which includes the preform first section 15 fitted with window compartments 13 and 14 containing the light source 11 and detector 12, and connecting wires 11a and 12a, all secured into proper position. The coffin mold holds and retains the preform assembly in proper alignment, and allows insertion and removal of the preform assembly into and out of the main mold base for overmolding. Use of coffin molds thereby protects the sensor components from high base mold temperatures which could damage the components. Use of coffin molds also facilitates rapid loading of the base mold and removal of the completed overmolded sensor apparatus 10.

In order to provide a seal which is resistant to penetration by liquids between the preform first section 15 and the overmolded second section 19, without the need for the high temperatures required to achieve a total fusion bond of the two PVC surfaces, a mechanical bond is formed during the overmolding process. To accomplish this, in the preferred embodiment the preform first section 15 is provided with protuberances in the form of dovetail-shaped ribbing 20 extending from the majority of the periphery of the interior surface of the preform first section 15. Thus, when the overmolding operation is performed, the new injection molding (PVC) material flows around the dovetail-shaped ribbing 20 and physically forms a mechanical bond between the elements of the overmolded second section 19 which abut and overlap the ribbing elements 20 of the preform first section 15. As a result, a liquid-resistant seal or bond between the preform first section 15 and the overmolded second section 19 is formed during overmolding, sealing the sensor components within the resulting sensor apparatus 10. This seal, as formed during overmolding, prevents moisture from liquids used to disinfect (by wiping or immersion) the sensor apparatus 10 between patients or applications from contacting the sensor components enclosed within the sensor apparatus 10.

In an effort to further reduce costs, the mold for the preform first section 15 may be designed into the main mold base, such that the preforms are molded at the same time that the overmolding operation takes place.

While embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. A method of forming a molded pulse oximeter sensor apparatus utilizing an overmolding step, comprising:

supplying a preform first section having an interior surface and an exterior surface;

securing oximeter sensing components in a fixed configuration to said interior surface of said preform first section so that the position of said sensing components will be maintained during overmolding; and utilizing injection molding to overmold a second section which is bonded to said preform first section such that said sensing components are enclosed between said preform first section and said overmolded second section, and wherein the bond between said preform first section and said overmolded second section at their peripheries comprises a mechanical bond of overlapping elements.

2. The method of claim 1 wherein said mechanical bond of overlapping elements comprises protuberances extending from the surface of said preform first section along its periphery, said protuberances having a shape such that said protuberances are wider at a point more distant from the surface of said preform first section than at a point closer to the surface of said preform first section, and wherein said overmolded second section is formed surrounding said protuberances.

3. The method of claim 2 wherein said protuberances have a dovetail shape such that the narrowest portion of the dovetail is closer than its widest portion to the surface of said preform first section from which said protuberances extend.

4. The method of claim 2 wherein said protuberances extend perpendicularly from the surface of said preform first section.

5. The method of claim 1 wherein said bond formed during overmolding between said preform first section and said overmolded second section is resistant to penetration by liquid.

6. The method of claim 1 wherein said bond formed during overmolding between said preform first section and said overmolded second section prevents liquid from penetrating the bond and contacting the sensing components positioned between said first and second sections.

7. The method of claim 1 wherein said oximeter sensing components comprise a light source, a detector, and connecting wires.

8. The method of claim 1 further comprising supplying window compartments which interlock into position in cavities contained in said preform first section and which extend to the exterior surface of said preform first section, and into which window compartments the light source and detector sensing components are secured.

9. The method of claim 8 wherein said window compartments form a seal with said preform first section which is resistant to penetration by liquid.

10. The method of claim 1 wherein coffin molds are utilized to hold said preform first section and oximeter sensing components during the overmolding step, and wherein said coffin mold is inserted into the base mold during overmolding.

* * * * *